United States Patent
Aranyi et al.

(10) Patent No.: US 7,709,489 B2
(45) Date of Patent: May 4, 2010

(54) IMIDAZOQUINOLINE DERIVATIVES AS ADENOSINE A3 RECEPTOR LIGANDS

(75) Inventors: Peter Aranyi, Budapest (HU); Laszlo Balazs, Budapest (HU); Maria Balogh, Budapest (HU); Sandor Batori, Budapest (HU); Lajos T. Nagy, Budapest (HU); Geza Timari, Budapest (HU); Kinga Boer, Budapest (HU); Zoltan Kapui, Budapest (HU); Endre Mikus, Budapest (HU); Katalin Gerber, Budapest (HU); Judit Vargane Szeredi, Budapest (HU); Katalin Urban-Szabo, Budapest (HU); Erzsebet Walcz, Budapest (HU)

(73) Assignee: sanofi-aventis, Paris (FR)

( * ) Notice: Subject to any disclaimer, the term of this patent is extended or adjusted under 35 U.S.C. 154(b) by 120 days.

(21) Appl. No.: 12/140,512

(22) Filed: Jun. 17, 2008

(65) Prior Publication Data

US 2008/0255110 A1 Oct. 16, 2008

Related U.S. Application Data

(60) Division of application No. 11/130,429, filed on May 16, 2005, now Pat. No. 7,419,977, which is a continuation of application No. PCT/HU03/00095, filed on Nov. 11, 2003.

(30) Foreign Application Priority Data

Nov. 15, 2002 (HU) .................................... 0203976

(51) Int. Cl.
*A61K 31/496* (2006.01)
*C07D 403/14* (2006.01)
*C07D 403/06* (2006.01)
(52) U.S. Cl. ................................ 514/254.06; 544/370
(58) Field of Classification Search ............ 514/254.06; 544/370
See application file for complete search history.

(56) References Cited

U.S. PATENT DOCUMENTS 4,291,033 A 9/1981 Barnes et al.
4,333,934 A 6/1982 Barnes et al.
4,474,784 A 10/1984 Barnes et al.
4,644,002 A 2/1987 Barnes et al.
6,376,521 B1 4/2002 Jacobson et al.
6,407,236 B1 6/2002 Baraldi et al.
6,686,343 B1 2/2004 Okamura et al.
2002/0094974 A1 7/2002 Castelhano et al.
2004/0186133 A1 9/2004 Aranyl et al.
2005/0070566 A1 3/2005 Aranyl et al.
2005/0234056 A1 10/2005 Aranyi et al.

FOREIGN PATENT DOCUMENTS

WO WO 03/053968 7/2003

OTHER PUBLICATIONS

Ager, et al., Synthesis and oral antiallergic activity of carboxylic acids derived from imidazo[2,1-c][1,4]benzoxazines, imidazo[1,2-a]quinolines, imidazo[1,2-a]quinoxalines, imidazo[1,2-a]quinoxalinones, pyrrolo[1,2-a]quinoxalinones, pyrrolo[2,3-a]quinoxalinones, and imidazo[2,1-b]benzothiazoles , J. of Medicinal Chem.; 31:6; 1988; pp. 1098-1115.

*Primary Examiner*—Rebeeca L Anderson
(74) *Attorney, Agent, or Firm*—Brian R. Morrill

(57) ABSTRACT

This invention is directed to a compound of formula (I),

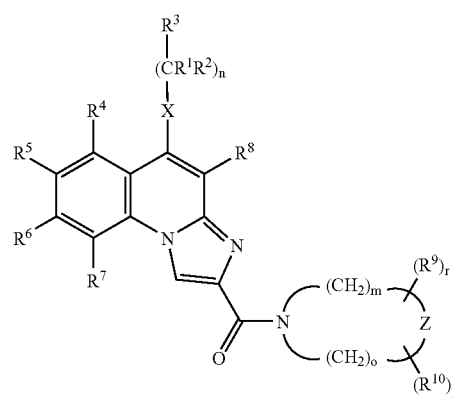

wherein $R^1, R^2, R^3, R^4, R^5, R^6, R^7, R^8, R^9, R^{10}$, X, Z, m, n, o, p and r are as defined herein, its preparation, pharmaceutical composition and use as an adenosine $A_3$ receptor ligand preferably an antagonist.

12 Claims, No Drawings

IMIDAZOQUINOLINE DERIVATIVES AS ADENOSINE A3 RECEPTOR LIGANDS

This application is a divisional of application Ser. No. 11/130,429, filed May 16, 2005, now U.S. Pat. No. 7,419,977, which is a continuation of International Application No. PCT/HU2003/00095, filed Nov. 11, 2003.

FIELD OF THE INVENTION

The present invention relates to the adenosine $A_3$ receptor ligands of the general formula (I),

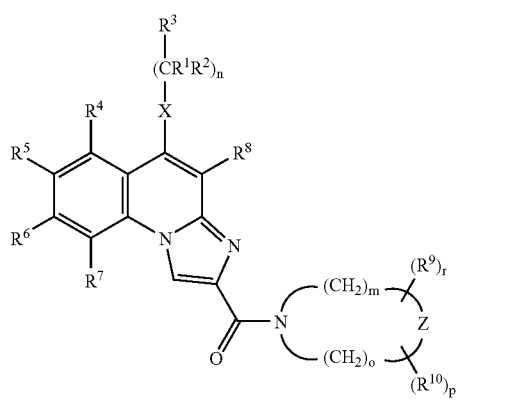

within those preferably to the antagonists, as well as to their salts, solvates and isomers, to the pharmaceutical compositions containing them, to the use of the compounds of the general formula (I) and their salts, solvates and isomers, and to the preparation of the compounds of the general formula (I) and their salts, solvates and isomers.

BACKGROUND OF THE INVENTION

Adenosine is a well-known component of several endogenous molecules (ATP, $NAD^+$, nucleic acids). Besides, it plays an important regulatory role in many physiological processes. The effect of adenosine on heart function was discovered already in 1929. (Drury and Szentgyörgyi, J Physiol 68:213, 1929). The identification of an increasing number of physiological functions mediated by adenosine and the discovery of new adenosine receptor subtypes give possibilities for therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for the inhibition of the adenylate cyclase by coupling to $G_i$ membrane protein, partly influences other second messenger systems. The $A_2$ receptor subtype can be subdivided into two further subtypes—$A_{2a}$ and $A_{2b}$, which stimulate the adenylate cyclase activity. The sequence of adenosine $A_3$ receptors have been recently identified from rat testis cDNA library. Later it was proved that it corresponds to a novel, functional adenosine receptor. The activation of the $A_3$ receptors is connected also with several second-messenger systems: inhibiting of adenylate cyclase, stimulating phospholipase C and D.

The adenosine receptors are found in several organs and regulate their functions. Both $A_1$ and $A_{2a}$ receptors play important role in the central nervous system and cardiovascular system. In the CNS, the adenosine inhibits the release of synaptic transmitters which effect is mediated by $A_1$ receptors. In the heart, also the $A_1$ receptors mediate the negative inotropic, chronotropic and dromotropic effects of adenosine. The adenosine $A_{2a}$ receptors, which are located in a relatively high amount in the striatum, display functional interaction with the dopamine receptors in regulating the synaptic transmission. The $A_{2a}$ adenosine receptors on endothelial and smooth muscle cells are responsible for adenosine-induced vasodilation.

On the basis of mRNA identification, the $A_{2b}$ adenosine receptors are widely distributed in different tissues. They have been identified almost in every cell type, but its expression is the highest in the intestine and the bladder. This subtype probably also has important regulatory function in the regulation of the vascular tone and plays a role in the function of mast cells.

Contrary to $A_1$ and $A_{2a}$ receptors, where the tissue distribution was detected on the protein level, the presence of $A_{2b}$ and $A_3$ receptors was detected on the basis of their mRNA level. Expression levels for $A_3$ adenosine receptors are rather low compared to other subtypes and are highly species dependent. $A_3$ adenosine receptors are expressed primarily in the central nervous system, testis and immune system, and appear to be involved in the modulation of mediator release from mast cells in immediate hypersensitivity reaction.

The $A_3$ antagonists published so far in the literature belong to the groups of flavonoides, 1,4-dihydropyridine derivatives, triazoloquinazolines, thiazolonaphthyridines and thiazolopyrimidines. The present invention relates to a novel type of effective $A_3$ antagonists, which have the aminoquinoline structure.

For therapeutic use it is essential to ensure that the molecule does not bind, or bind only in the case of very high concentration, to the $A_1$, $A_{2a}$ and $A_{2b}$ sub-types of the adenosine receptor. Our present invention relates to the compounds of the general formula (I) as well as their salts, solvates and isomers, which have great selectivity for the $A_3$ sub-type of the adenosine receptor.

Our aim was to prepare $A_3$ ligands, within them preferably antagonists, first of all with quinoline structure, which exert strong antagonistic effect and high selectivity for the $A_3$ receptor, i.e. they inhibit the $A_3$ receptor in much lower concentration than they inhibit the $A_1$, $A_{2a}$ and $A_{2b}$ receptors. Further aims were to have stability, bioavailability, therapeutic index and toxicity data, enabling these new compounds to develop into drug substances, and that the new compounds possess favourable enteric absorption to be applied orally.

SUMMARY OF THE INVENTION

We have found that the compounds of the general formula (I), wherein
- $R^1$ stands for hydrogen atom or a straight or branched $C_{1-4}$ alkyl group;
- $R^2$ stands for hydrogen atom or a straight or branched $C_{1-4}$ alkyl group;
- $R^3$ stands for hydrogen atom, or a straight or branched $C_{1-4}$ alkyl group, $C_{3-6}$ cycloalkyl group, a phenyl-, thienyl-, or furyl group, optionally substituted with one or more straight or branched $C_{1-4}$ alkyl group, straight or branched $C_{1-4}$ alkoxy group, or halogen atom; a six- or five-membered heteroaromatic ring containing one, two or three nitrogen atoms, or a five-membered heteroaromatic ring containing one nitrogen atom and one oxygen atom, or one nitrogen atom and one sulphur atom, optionally substituted with one or more straight or branched $C_{1-4}$ alkyl group, straight or branched $C_{1-4}$ alkoxy group or halogen atom;
- $R^4$, $R^5$, $R^6$ and $R^7$ independently stand for hydrogen atom, straight or branched $C_{1-4}$ alkyl group, straight or branched $C_{1-4}$ alkoxy group, hydroxy group or halogen atom, or $R^4$ and $R^7$ stand for hydrogen atom and $R^5$ and $R^6$ form together a methylenedioxy group;
- $R^8$ stands for hydrogen atom or a cyano group, aminocarbonyl group, $C_{1-4}$ alkoxycarbonyl group, or carboxy group;
- $R^9$ and $R^{10}$ independently stand for hydrogen atom, straight or branched $C_{1-4}$ alkyl group, $C_{3-6}$ cycloalkyl group.
- X stands for —$CH_2$— group, —NH— group, —$NR^{11}$— group, or sulphur atom, oxygen atom, —$SO_2$— or —SO—, wherein $R^{11}$ stands for straight or branched $C_{1-4}$ alkyl group or $C_{3-6}$ cycloalkyl group;
- Z means oxygen atom, sulphur atom, —NH— group or —$NR^{12}$— group, wherein $R^{12}$ stands for straight or branched $C_{1-4}$ alkyl group or $C_{3-6}$ cycloalkyl group;
- m stands for zero, 1, 2 or 3;
- n stands for zero, 1 or 2;
- stands for zero, 1, 2 or 3;
- p stands for zero or 1,
- r stands for zero or 1, with the proviso that at least one of m and o is different from zero, and their salts, solvates, and isomers, as well as the salts and solvates thereof fulfil the above criteria.

DETAILED DESCRIPTION OF THE INVENTION

Definition of Terms

Detailed meanings of the above listed substituents are as follows:

By a straight or branched $C_{1-4}$ alkyl group we mean methyl-, ethyl-, propyl-, isopropyl-, butyl-, isobutyl-, secondary-butyl-, terciary-butyl-, preferably ethyl- or methyl group.

By a straight or branched $C_{1-4}$ alkoxy group we mean methoxy-, ethoxy-, propoxy-, isopropoxy-, butoxy-, isobutoxy-, secondary-butoxy-, terciary-butoxy-, preferably ethoxy- or methoxy group.

By a $C_{3-6}$ cycloalkyl group we mean cyclopropyl-, cyclobutyl-, cyclopentyl- or cyclohexyl group.

The heteroaromatic ring containing one or two or three nitrogen atoms means pyrrole, imidazole, pyrazole, 1,2,3-triazole, 1,2,4-triazole, pyridine, pyrimidine, pyridazine, pyrazine and 1,3,4-triazine ring. The ring is optionally substituted by a $C_{1-4}$ alkyl group, or alkoxy group or by a halogen atom.

The heteroaromatic ring containing one nitrogen atom and one oxygen or one sulphur atom means oxazole, isoxazole, thiazole, isothiazole ring. The ring is optionally substituted by a $C_{1-4}$ alkyl group, or alkoxy group or by a halogen atom.

The —$(CH_2)_m$-Z-$(CH_2)_o$— group forms together with the nitrogen atom an oxaziridino-, diaziridino-, 1,2-diazetidino-, 1,3-diazetidino-, isoxazolidino-, oxazolidino-, imidazolidino-, pirazolidino-, thiazolidino-, morpholino-, piperazino-, or 4-methyl-piperazino-group, optionally substituted by a $C_{1-4}$ alkyl group or $C_{3-6}$ cycloalkyl group.

By salts of the compounds of the general formula (I) we mean salts given with inorganic and organic acids and bases. Preferred salts are those given with pharmaceutically accepted acids, as for instance hydrochloric acid, sulphuric acid, ethanesulphonic acid, tartaric acid, succinic acid, malic acid, citric acid, and with pharmaceutically accepted bases, as for instance sodium hydroxide, potassium hydroxide, ethanolamine.

By solvates we mean solvates given with various solvents, as for instance with water or ethanol.

Patient includes both human and other mammals.

Pharmaceutically effective amount is meant to describe an amount of compound or compounds according to the present invention effective in producing the desired therapeutic effect.

The compounds of the general formula (I) show geometric and optical isomerism, therefore the invention also relates to mixtures of the geometric isomers, to racemic or optically active geometric isomers, as well as to their salts and solvates.

Particular or Preferred Embodiments

A favoured group of the compounds of the general formula (I)

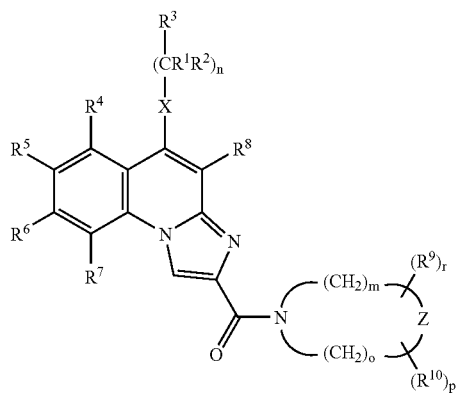

(I)

are those, wherein $R^1$ stands for hydrogen atom or a straight or branched $C_{1-4}$ alkyl group;

$R^2$ stands for hydrogen atom or a straight or branched $C_{1-4}$ alkyl group;

$R^3$ stands for hydrogen atom, or a straight or branched $C_{1-4}$ alkyl group, $C_{3-6}$ cycloalkyl group, a phenyl-, thienyl-, or furyl group, optionally substituted with one or more straight or branched $C_{1-4}$ alkyl group, straight or branched $C_{1-4}$ alkoxy group, or halogen atom;

$R^4$, $R^5$, $R^6$ and $R^7$ independently stand for hydrogen atom, straight or branched $C_{1-4}$ alkyl group, straight or branched $C_{1-4}$ alkoxy group, hydroxy group or halogen atom, or $R^4$ and $R^7$ stand for hydrogen atom and $R^5$ and $R^6$ form together a methylenedioxy group;

$R^8$ stands for hydrogen atom or a cyano group, aminocarbonyl group, $C_{1-4}$ alkoxycarbonyl group, or carboxy group;

$R^9$ and $R^{10}$ independently stand for hydrogen atom, straight or branched $C_{1-4}$ alkyl group, or $C_{3-6}$ cycloalkyl group.

X stands for —$CH_2$— group, —NH— group, —$NR^{11}$— group, or sulphur atom, oxygen atom, —$SO_2$— or —SO—, wherein $R^{11}$ stands for straight or branched $C_{1-4}$ alkyl group or $C_{3-6}$ cycloalkyl group;

Z means oxygen atom, sulphur atom, —NH— group or —$NR^{12}$— group, wherein $R^{12}$ stands for straight or branched $C_{1-4}$ alkyl group or $C_{3-6}$ cycloalkyl group;

m stands for zero, 1, 2 or 3;

n stands for zero, 1 or 2;

o stands for zero, 1, 2 or 3;

p stands for zero or 1, r stands for zero or 1, with the proviso that at least one of m and o is different from zero, and their salts, solvates, and optically active isomers, as well as the salts and solvates thereof.

A more favoured group of the compounds of the general formula (I)

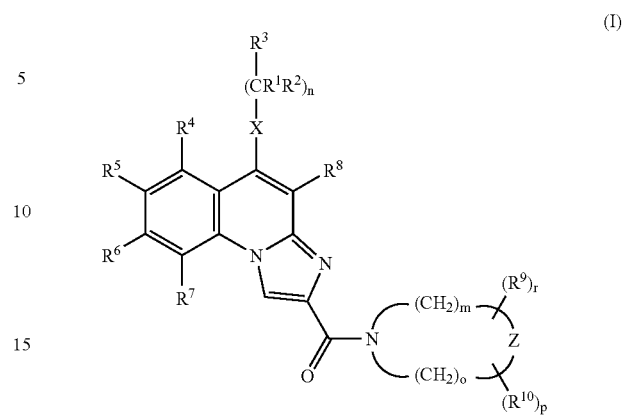

(I)

are those wherein $R^1$ stands for hydrogen atom or methyl group;

$R^2$ stands for hydrogen atom or methyl group;

$R^3$ stands for phenyl-, thienyl-, or furyl group;

$R^4$, $R^5$, $R^6$ and $R^7$ independently stand for hydrogen atom, straight or branched $C_{1-4}$ alkyl group, straight or branched $C_{1-4}$ alkoxy group, hydroxy group or halogen atom, or $R^4$ and $R^7$ stand for hydrogen atom and $R^5$ and $R^6$ form together a methylenedioxy group;

$R^8$ stands for hydrogen atom or a cyano group;

$R^9$ and $R^{10}$ stand for hydrogen atom, methyl-ethyl-, or cyclopropyl group.

X stands for —NH— group or oxygen atom;

Z means oxygen atom, sulphur atom, —NH— group or —$NR^{12}$— group, wherein $R^{12}$ stands for straight or branched $C_{1-4}$ alkyl group or $C_{3-6}$ cycloalkyl group; and m stands for 2;

n stands for 1;

o stands for 2;

p stands for zero;

r stands for zero, and their salts, solvates, and isomers, as well as the salts and solvates thereof.

Especially favoured are the following compounds which fulfil the above criteria:

1-(9-Benzylamino-10-cyano-imidazo[1,2-a]quinoline-2-carbonyl)-4-methylpiperazine 1-(9-Benzylamino-10-cyano-imidazo[1,2-a]quinoline-2-carbonyl)morpholine 1-(9-Furfurylamino-10-cyano-imidazo[1,2-a]quinoline-2-carbonyl)-4-methylpiperazine 1-(9-Furfurylamino-10-cyano-imidazo[1,2-a]quinoline-2-carbonyl)piperazine 1-(9-Furfurylamino-10-cyano-imidazo[1,2-a]quinoline-2-carbonyl)morpholine 1-(9-Thienylamino-10-cyano-imidazo[1,2-a]quinolin-2-carbonyl)morpholine 1-(9-Thienylamino-10-cyano-imidazo[1,2-a]quinoline-2-carbonyl)piperazine and their salts, solvates and isomers, as well as the salts and solvates thereof.

The present invention also relates to pharmaceutical compositions containing as active principles the compounds of the general formula (I) or their isomers, salts and solvates, which are preferably oral compositions, but inhalable, parenteral and transdermal formulations are also subjects of the invention. The above pharmaceutical compositions may be solids or liquids, such as tablets, pellets, capsules, patches, solutions, suspensions or emulsions. The solid compositions, first of all tablets and capsules are preferred.

The above pharmaceutical compositions are prepared by applying usual pharmaceutical auxiliary materials and by using standard methods.

The compounds of the general formula (I) can be used for the treatment of pathologies, where $A_3$ receptor plays a role in the development of the disease.

The compounds having selective activity on the $A_3$ receptor can be used in the therapeutic and/or preventive treatment of disfunctions of the heart, kidney, respiratory system, central nervous system. They block the protective effect of adenosine on the growing tumoric cells, prevent degranulation of the mast cells, hinder the formation of cytokines, decrease the inner pressure in the eye, prevent the TNFα liberation, hinder the migration of the eozinofil and neutrofil granulocytes and of other inflammation cells, prevent the constriction of the trachea and prevent the blood plasma to pass through the wall of the blood-vessel.

Based on the above effects, adenosine $A_3$ receptor antagonists may be therapeutically useful as antiinflammatory, antiasthmatic, antiischemic, antidepressive, antiarrhythmic, kidney function protective, tumor preventing, antiparkinson and cognitive function stimulating drugs. They may also be useful in the treatment or prevention of the following diseases: injury of the heart muscle during reperfusion, chronic obstructive pulmonary disease (COPD), adult respiratory insufficiency (ARDS)—including chronic bronchitis, pulmonary emphysema or difficult breathing, allergic reactions (e.g. rhinitis, poison ivy-induced responses, nettle-rush, scleroderma, arthritis), other autoimmune diseases, inflammatory bowel diseases, Addison disease, Crohn disease, psoriasis, diseases of the joints, hypertonia, abnormal neurological functions, glaucoma and diabetes (K. N. Klotz, Naunyn-Schmiedberg's Arch. Pharmacol. 362:382, 2000; P. G. Baraldi és P. A. Borea, TiPS 21:456, 2000).

The compounds of the present invention can favourably be used in the treatment of disfunctions like asthma, COPD and ARDS, glaucoma, tumor, allergic and inflammatory diseases, ischemic, hypoxia, arrhythmia of the heart, and diseases of the kidney.

The present invention relates furthermore to the use of the compounds of the general formula (I) in the treatment of the above pathologies. The suggested daily dose is 0.1-1000 mg active ingredient, depending on the nature and severeness of the disease and on the sex, weight etc. of the patient.

A further subject of the invention is the preparation of the compounds of the general formula (I).

The substituents in the formulae of the intermediates of the general formulae (II), (III), (IV), (V), (VI), (VII) and (VIII) have the meanings as defined above.

In the process according to our invention the compounds of the general formula (VIII)

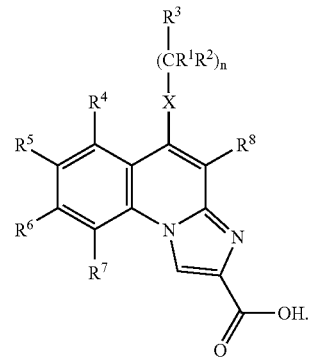

are acylated with the acids or their reactive derivatives of the general formula (II),

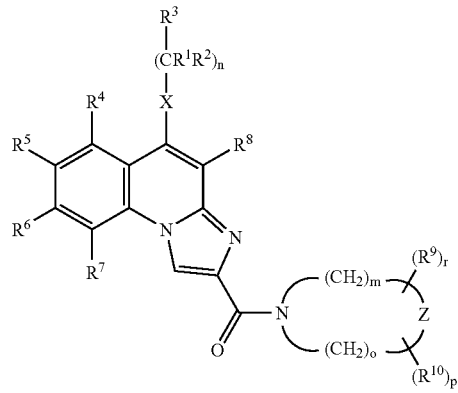

by applying an acylation method known in the organic chemistry. As for acylating agent, acid halogenides or mixed anhydrides are preferably used. The resulting compound of the general formula (I)

(I)

is—if desired—transformed into one of its salts or solvates, or liberated from its salt or solvate and separated into its geometric or optical isomers.

The substituents of the compounds of the general formula (I) may be transformed into each other, by known methods.

The mixed anhydride used for the acylation reaction can be prepared with pivaloyl chloride, favourably by using organic bases dissolved in chloroform, preferably by using triethylamine, but other methods known in the organic chemistry can also be applied. Acylation can be performed in a broad temperature range, preferably between 0° C. and 100° C.

The intermediates of the general formula (II)

II wherein the meanings of $R^1$, $R^2$, $R^3$, $R^4$, $R^5$, $R^6$, $R^7$, $R^8$, X and n are as defined above—can be obtained by several known methods, for example by the method demonstrated in Scheme 1.
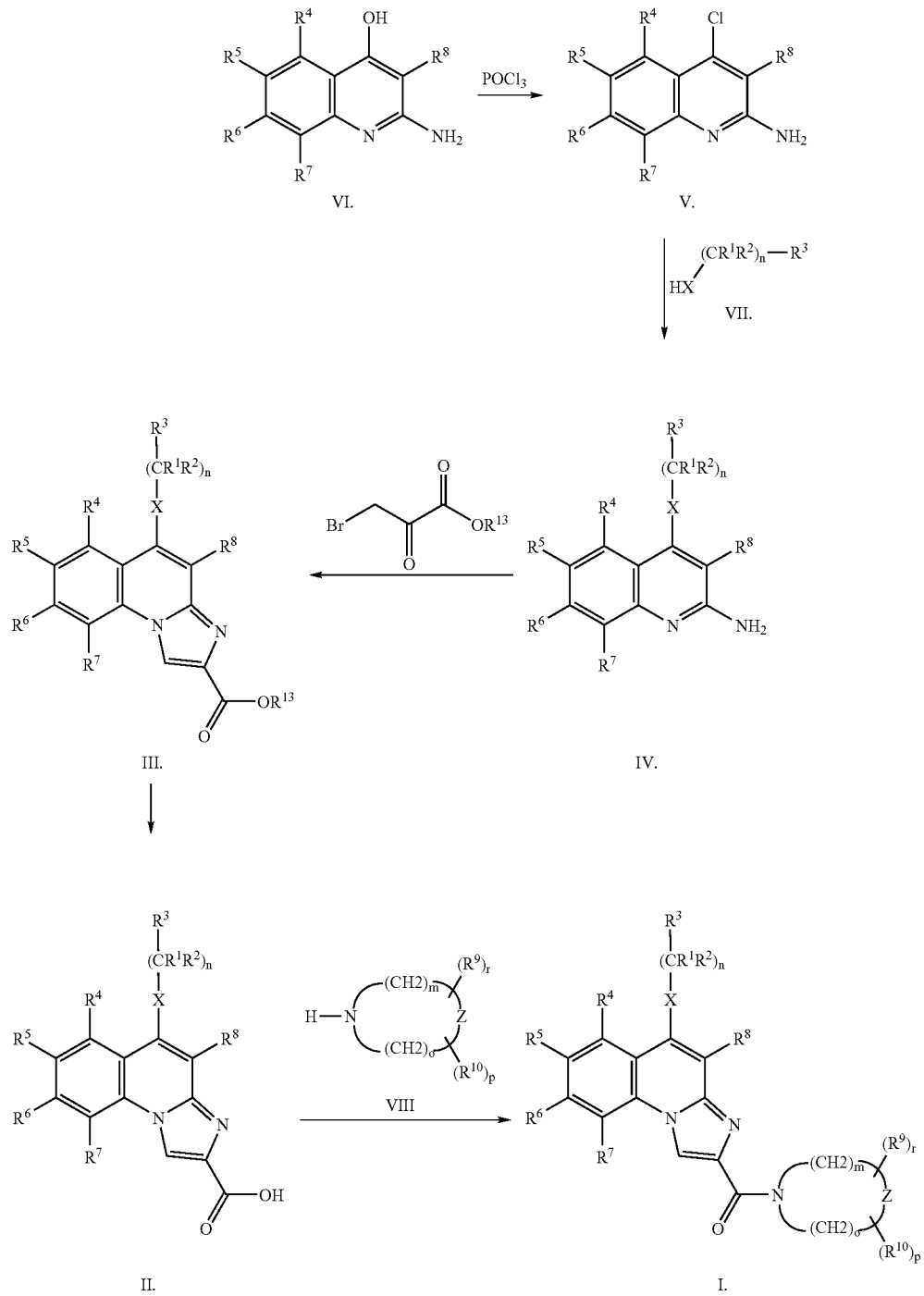

starting from the compounds of the general formula (III)

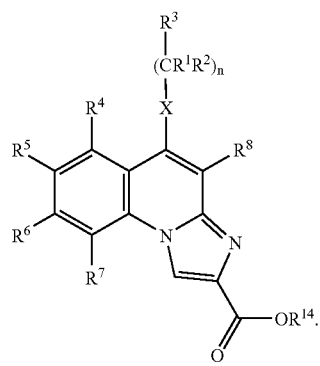

and applying a hydrolysis method known in the organic chemistry. As for hydrolysing agent alkali hydroxides can be used, but other compounds promoting the hydrolysis of esters can also be applied.

The compounds of the general formula (III)

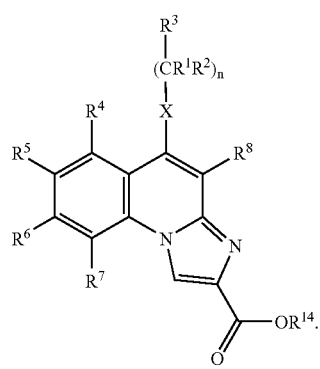

wherein the meanings of $R^1$, $R^2$, $R^3$, $R^4$, $R^5$, $R^6$, $R^7$, $R^8$, X and n are as defined above, and $R^{13}$ means a $C_{1-4}$ alkyl group, can be prepared from the compounds of the formula (IV)

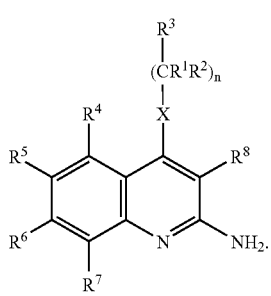

by using methods known per se. (I. R. Ager and R. Westwood, J. Med. Chem. 31, 1098, 1988).

The compounds of the general formula (IV)

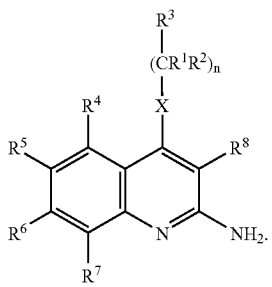

wherein the meanings of $R^1$, $R^2$, $R^3$, $R^4$, $R^5$, $R^6$, $R^7$, $R^8$, X and n are as defined above, can be prepared from the compounds of the formula (V)

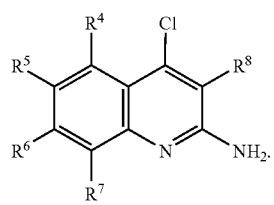

by using methods known per se (Nan Zhang, Bioorg. and Med. Chem. Lett., 10, 2825, 2000).

The compounds of the general formula (V)

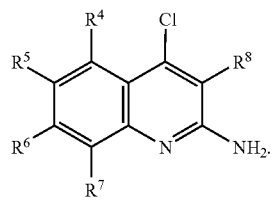

wherein the meanings of $R^4$, $R^5$, $R^6$, $R^7$ and $R^8$ are as defined above, can be prepared from the compounds of the formula (VI)

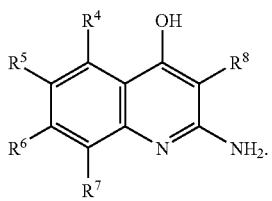

by using methods known per se (D. L. Leysen, J. Heterocyclic Chem., 24, 1611, 1987).

The compounds of the general formula (VI)

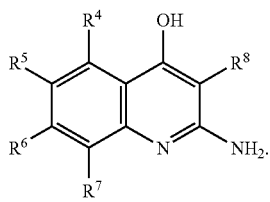

wherein the meanings of $R^4$, $R^5$, $R^6$, $R^7$ and $R^8$ are as defined above, can be prepared by using methods known per se (Pfizer (Inc) U.S. Pat. No. 4,175,193).

The compounds of the invention, of the general formulae (I), (II), (III), (IV) and (V), their preparation and biological activity are demonstrated by the following Examples, without limiting the claims to the Examples.

EXAMPLES

Example 1

1-(9-Benzylamino-10-cyano-imidazo[1,2-a]quinoline-2-carbonyl)-4-methyl-piperazine In the general formula (I) $R^1$ and $R^2$ stand for hydrogen atom, $R^3$ for phenyl group, $R^4$, $R^5$, $R^6$ and $R^7$ for hydrogen atom, $R^5$ for cyano group, $R^{12}$ for methyl group, X means —NH— group, Z means nitrogen atom, the value of n is 1, the value of m and o is 2, and the value of r and p is 0.

a.) 2-Amino-3-cyano-4-chloroquinoline

The mixture of 10 g of 2-amino-3-cyano-4-hydroxyquinoline and 15 ml of phosphoryl chloride is heated under stirring at 110° C. The reaction mixture is cooled down, poured onto 100 ml of ice-water and neutralized with 60 ml of 10% sodium hydroxide solution. The resulting yellow precipitate is filtered off, washed with 50 ml of water. After drying 7.5 g of the title compound is obtained, mp.: 210° C.

NMR, δH (400 MHz, DMSO-d$_6$): 7.21 ppm, (s, 2H, NH2), 7.35-7.40 ppm, (dd, 1H, 6-H), 7.53-7.57 ppm, (d, 1H, 5-H), 7.70-7.75 ppm, (dd, 1H, 7-H), 7.93-7.98 ppm, (d, 1H, 8-H)

b.) 2-Amino-3-cyano-4-benzylaminoquinoline 5 g of 2-amino-3-cyano-4-chloroquinoline and 11 ml of benzylamine are heated under stirring at 130° C. The reaction mixture is poured onto 50 ml of water, the resulting precipitate is filtered off, washed with 50 ml of water. The pale-yellow precipitate is recrystallized from 25 ml of dimethyl-formamide to obtain 5.2 g of the title compound. Mp.: 206° C.

NMR, $δ_H$ (400 MHz, DMSO-d$_6$): 5.02-5.03 ppm, (d, 2H, N—CH$_2$), 6.22 ppm, (s, 2H, NH$_2$), 7.14-7.16 ppm, (dd, 1H, 6-H), 7.24-7.26 ppm, (dd, 1H, 5-H), 7.30 ppm, (s, 5H, Ph), 7.50-7.52 ppm, (d, 1H, 7-H), 8.16-8.19 ppm, (d, 1H, 8-H), 8.30-8.33 ppm, (t, 1H, NH).

Using 2-aminomethylpyridine or 3-aminomethylpyridine or 4-aminomethylpyridine instead of benzylamine, the appropriate compounds of the general formula IV can be obtained.

c. Ethyl 9-benzylamino-10-cyano-imidazo[1,2-a]quinoline-2-carboxylate monohydrate To the solution of 2.74 g of 2-amino-3-cyano-4-benzylaminoquinoline in 100 ml of abs. Ethanol, 2.14 g of ethyl bromopyruvate is added under stirring at 70° C. The reaction mixture is heated under reflux for 2 hours, the resulting precipitate is filtered off. The white crystals are recrystallized from 120 ml of acetonitrile. 1.1 g of the title compound is obtained, m.p.: 112-114° C.

NMR, $δ_H$ (400 MHz, DMSO-d$_6$): 1.32 ppm (t, 3H, COOCH$_2$CH$_3$), 4.30 ppm (q, 2H, COOCH$_2$CH$_3$), 5.09 ppm (d, 2H, PhCH$_2$), 7.25-7.38 ppm (m, 5H), 7.64-7.67 ppm (m, 1H), 7.85-7.88 ppm (m, 1H), 8.43-8.53 ppm (m, 3H), 9.04 ppm (s, 1H, 3-H).

d. 9-Benzylamino-10-cyano-imidazo[1,2-a]quinoline-2-carboxylic acid

The mixture of 2.71 g of ethyl 9-benzylamino-10-cyano-imidazo[1,2-a]quinoline-2-carboxylate monohydrate, 42 ml of ethanol and 40 ml of 10% sodium hydroxide is stirred at 25° C. for 6 hours. To the thick suspension 100 ml of water is added and the pH of the mixture is adjusted to pH=3 with 96% acetic acid. The pale yellow crystals are filtered off, washed 3 times with 25 ml of water, and dried. 2.3 g title compound is obtained, m.p.: 178-182° C.

NMR, $δ_H$ (200 MHz, DMSO-d$_6$): 5.09 ppm (d, 2H, PhCH$_2$), 7.22-7.40 ppm (m, 5H), 7.59-7.67 ppm (m, 1H), 7.81-7.89 ppm (m, 1H), 8.37-8.54 ppm (m, 3H), 8.90 ppm (s, 1H, 3-H).

e. 1-(9-Benzylamino-10-cyano-imidazo[1,2-a]quinoline-2-carbonyl)-4-methylpiperazine To the solution of 1.71 g of 9-benzylamino-10-cyano-imidazo[1,2-a]quinoline-2-carboxilic acid and 0.8 ml of triethylamine in 15 ml of chloroform, the solution of 0.6 g of pyvaloyl chloride in 10 ml of chloroform is added dropwise, under stirring, at 5° C., in a period of 15 minutes. The reaction mixture is stirred at 5° C. for 1 hour, then the mixture of 0.5 g of N-methylpiperazine, 10 ml of chloroform and 0.8 ml of triethylamine is added to it. The mixture is stirred at 25° C. for 7 hours, diluted with 100 ml of chloroform, extracted consecutively with 50 ml of water, 50 ml of 5% sodium hydrogen carbonate solution and 50 ml of water, dried on sodium sulfate and concentrated in vacuo. The pale yellow crystalline material is recrystallized from 6 ml of N,N-dimethylformamide. 0.6 g of the title compound is obtained, m.p.: 217° C.

NMR, $δ_H$ (400 MHz, DMSO-d$_6$): 2.17 ppm (s, 3H), 2.24 ppm (m, 4H), 3.57 ppm (m, 2H), 4.11 ppm (m, 2H), 5.08 ppm (d, 2H, PhCH$_2$), 7.23-7.38 ppm (m, 5H), 7.62-7.65 ppm (m, 1H), 7.83-7.87 ppm (m, 1H), 8.36-8.42 ppm (m, 2H), 8.50-8.52 ppm (m, 1H), 8.80 ppm (s, 1H, 3-H).

Example 2

1-(9-Benzylamino-10-cyano-imidazo[1,2-a]quinoline-2-carbonyl)morpholine

In the general formula (I) $R^1$ and $R^2$ stand for hydrogen atom, $R^3$ for phenyl group, $R^4$, $R^5$, $R^6$ and $R^7$ for hydrogen atom, $R^8$ for cyano group, X means —NH— group, Z means oxygen atom, the value of n is 1, the value of m and o is 2, and the value of r and p is 0.

To the mixture of 1.71 g of 9-benzylamino-10-cyano-imidazo[1,2-a]quinoline-2-carboxilic acid and 0.8 ml of triethylamine in 15 ml of chloroform, the solution of 0.6 g of pyvaloyl chloride in 10 ml of chloroform is added under stirring at 5° C., in a period of 15 minutes. The reaction mixture is stirred at 5° C. for 1 hour, then the mixture of 0.45 g of morpholine, 10 ml of chloroform and 1.6 ml of triethylamine is added to it. The mixture is stirred at 25° C. for 3 hours, then treated as described in the previous example. The resulting pale yellow crystals are recrystallised from 10 ml of N,N-dimethylformamide, to obtain 0.55 g of the title compound, m.p.: 279° C.

NMR, $\delta_H$ (400 MHz, DMSO-$d_6$): 3.6 ppm (m, 6H), 4.2 ppm (m, 2H), 5.08 ppm (d, 2H, PhCH$_2$), 7.23-7.38 ppm (m, 5H), 7.62-7.65 ppm (m, 1H), 7.84-7.87 ppm (m, 1H), 8.37-8.39 ppm (m, 2H), 8.50-8.53 ppm (m, 1H), 8.75 ppm (s, 1H, 3-H).

Example 3

1-(9-Furfurylamino-10-cyano-imidazo[1,2-a]quinoline-2-carbonyl)-4-methylpiperazine In the general formula (I) $R^1$ and $R^2$ stand for hydrogen atom, $R^3$ for 2-furyl group, $R^4$, $R^5$, $R^6$ and $R^7$ for hydrogen atom, $R^8$ for cyano group, $R^{12}$ for methyl group, X means —NH— group, Z means nitrogen atom, the value of n is 1, the value of m and o is 2, and the value of r and p is 0.

a. 2-Amino-3-cyano-4-furfurylaminoquinoline 10 g of 2-amino-3-cyano-4-chloroquinoline is heated with 19 g of furfurylamine at 120° C. for 3 hours. The reaction mixture is cooled to 25° C. and mixed 6 times with 50 ml of water. The crystals are filtered off and dried. The resulting product is recrystallized from 60 ml of N,N-dimethylformamide, to obtain 5.8 g of the title compound, m.p.: 206° C.

NMR, $\delta_H$ (200 MHz, DMSO-$d_6$): 4.98 ppm (d, 2H, Furyl-CH$_2$), 6.29 ppm (s, 2H), 6.35-6.42 ppm (m, 2H), 7.10-7.18 ppm (m, 1H), 7.31-7.35 ppm (m, 1H), 7.47-7.60 ppm (m, 2H), 8.13-8.20 ppm (m, 2H).

b. Ethyl 9-furfurylamino-10-cyano-imidazo[1,2-a]quinoline-2-carboxylate monohydrate To the solution of 2.64 g of 2-amino-3-cyano-4-furfurylaminoquinoline in 100 ml of abs. ethanol, 2.14 g of ethyl bromopyruvate is added at 70° C. under stirring. The reaction mixture is heated under reflux for 2 hours and the precipitated crystals are filtered off, to obtain 1.15 g of the title compound. M.p.: 242-245° C.

NMR, $\delta_H$ (200 MHz, DMSO-$d_6$): 1.33 ppm (t, 3H, COOCH$_2$CH$_3$), 4.31 ppm (q, 2H, COOCH$_2$CH$_3$), 5.05 ppm (d, 2H, Furyl-CH$_2$), 6.40-6.43 ppm (m, 2H), 7.58-7.66 ppm (m, 2H), 7.80-7.88 ppm (m, 1H), 8.31 ppm (t, 1H), 8.41-8.45 ppm (m, 2H), 9.04 ppm (s, 1H, 3H).

c. 9-Furfurylamino-10-cyano-imidazo[1,2-a]quinoline-2-carboxylic acid

The mixture of 2.52 g of ethyl 9-furfurylamino-10-cyano-imidazo[1,2-a]quinoline-2-carboxylate monohydrate, 40 ml of ethanol and 33 ml of 10% sodium hydroxide is stirred at 25° C. for 3 hours. To the thick suspension 80 ml of water is added and with 96% acetic acid the mixture acidified to pH=3. The pale yellow crystals are filtered off, washed 3 times with 25 ml of water and dried. 2.32 g of the title compound is obtained, m.p.: 180-185° C.

NMR, $\delta_H$ (200 MHz, DMSO-$d_6$): 5.05 ppm (d, 2H, Furyl-CH$_2$), 6.39-6.42 ppm (m, 2H), 7.56-7.64 ppm (m, 2H), 7.79-7.87 ppm (m, 1H), 8.27 ppm (t, 1H), 8.36-8.46 ppm (m, 2H), 8.93 ppm (s, 1H, 3-H).

d. 1-(9-Furfurylamino-10-cyano-imidazo[1,2-a]quinoline-2-carbonyl)-4-methylpiperazine To the mixture of 1.79 g of 9-furfurylamino-10-cyanoimidazo[1,2-a]quinoline-2-carboxylic acid and 0.8 ml of triethylamine in 15 ml of chloroform, the solution of 0.6 g of pyvaloyl chloride in 10 ml of chloroform is added dropwise, under stirring at 5° C., in a period of 15 minutes. The reaction mixture is stirred at 5° C. for 1 hour, then the mixture of 0.46 g of N-methylpiperazine, 10 ml of chloroform and 0.8 ml of triethylamine is added to it. The mixture is stirred at 25° C. for 3 hours, diluted with 100 ml of chloroform, extracted consecutively with 50 ml of water, 50 ml of 5% sodium hydrogen carbonate solution and 50 ml of water, dried over sodium sulfate and concentrated in vacuum. The pale yellow crystalline material is recrystallized from 50 ml of ethanol. 0.18 g of the title compound is obtained, m.p.: 237° C.

NMR, $\delta_H$ (200 MHz, DMSO-$d_6$): 2.17 ppm (s, 3H), 2.24 ppm (m, 4H), 3.57 ppm (m, 2H), 4.11 ppm (m, 2H), 5.05 ppm (d, 2H, Furyl-CH$_2$), 6.40-6.44 ppm (m, 2H), 7.57-7.65 ppm (m, 2H), 7.80-7.88 ppm (m, 1H), 8.23 ppm (t, 1H), 8.39-8.46 ppm (m, 2H), 8.81 ppm (s, 1H, 3-H).

Example 4

1-(9-Furfurylamino-10-cyano-imidazo[1,2-a]quinoline-2-carbonyl)piperazine

In the general formula (I) $R^1$ and $R^2$ stand for hydrogen atom, $R^3$ for 2-furyl group, $R^4$, $R^5$, $R^6$ and $R^7$ for hydrogen atom, $R^8$ for cyano group, X means —NH— group, Z means —NH— group, the value of n is 1, the value of m and o is 2, and the value of r and p is 0.

To the mixture of 1.79 g of 9-furfurylamino-10-cyano-imidazo[1,2-a]quinoline-2-carboxylic acid—obtained as described in Example 3 and 0.8 ml of triethylamine in 15 ml of chloroform, the solution of 0.6 g of pyvaloyl chloride in 10 ml of chloroform is added dropwise, under stirring at 5° C., in a period of 15 minutes. The reaction mixture is stirred at 5° C. for 1 hour, then the mixture of 0.46 g of piperazine, 10 ml of chloroform and 0.8 ml of triethylamine is added to it. The mixture is stirred at 25° C. for 3 hours, diluted with 100 ml of chloroform, extracted consecutively with 50 ml of water, 50 ml of 5% sodium hydrogen carbonate solution and 50 ml of water, dried over sodium sulfate and concentrated in vacuum. The pale yellow crystalline material is recrystallized from 50 ml of ethanol. 0.14 g of the title compound is obtained, m.p.: 239° C.

NMR, $\delta_H$ (200 MHz, DMSO-$d_6$): 2.7 ppm (m, 4H), 3.5 ppm (m, 2H), 4.05 ppm (m, 2H), 5.05 ppm (d, 2H, Furyl-CH$_2$), 6.40-6.44 ppm (m, 2H), 7.57-7.65 ppm (m, 2H), 7.80-7.88 ppm (m, 1H), 8.23 ppm (t, 1H), 8.39-8.46 ppm (m, 2H), 8.81 ppm (s, 1H, 3-H).

Example 5

1-(9-Furfurylamino-10-cyano-imidazo[1,2-a]quinoline-2-carbonyl)morpholine

In the general formula (I) $R^1$ and $R^2$ stand for hydrogen atom, $R^3$ for 2-furyl group, $R^4$, $R^5$, $R^6$ and $R^7$ for hydrogen atom, $R^5$ for cyano group, X means —NH— group, Z means oxygen atom, the value of n is 1, the value of m and o is 2, and the value of r and p is 0.

To the mixture of 1.79 g of 9-furfurylamino-10-cyano-imidazo[1,2-a]quinoline-2-carboxylic acid—obtained as described in Example 3—and 0.8 ml of triethylamine in 15 ml of chloroform, the solution of 0.6 g of pyvaloyl chloride in 10 ml of chloroform is added dropwise, under stirring at 5° C., in a period of 15 minutes. The reaction mixture is stirred at 5° C. for 1 hour, then the mixture of 0.66 g of morpholine, 10 ml of chloroform and 0.8 ml of triethylamine is added to it. The mixture is stirred at 25° C. for 3 hours, diluted with 100 ml of chloroform, extracted consecutively with 50 ml of water, 50 ml of 5% sodium hydrogen carbonate solution and 50 ml of water, dried over sodium sulfate and concentrated in vacuum. The pale yellow crystalline material is recrystallized from 50 ml of ethanol. 0.18 g of the title compound is obtained, m.p.: 267° C.

NMR, $\delta_H$ (200 MHz, DMSO-$d_6$): 3.6 ppm (m, 6H), 4.2 ppm (m, 2H), 5.05 ppm (d, 2H, Furyl-CH$_2$), 6.40-6.44 ppm (m, 2H), 7.57-7.65 ppm (m, 2H), 7.80-7.88 ppm (m, 1H), 8.23 ppm (t, 1H), 8.39-8.46 ppm (m, 2H), 8.81 ppm (s, 1H, 3-H).

Example 6

1-(9-Thienylamino-10-cyano-imidazo[1,2-a]quinoline-2-carbonyl)morpholine

In the general formula (I) $R^1$ and $R^2$ stand for hydrogen atom, $R^3$ for 2-tenyl group, $R^4$, $R^5$, $R^6$ and $R^7$ for hydrogen atom, $R^8$ for cyano group, X means —NH— group, Z means oxygen atom, the value of n is 1, the value of m and o is 2, and the value of r and p is 0.

a. 2-Amino-3-cyano-4-thienylaminoquinoline 10 g of 2-amino-3-cyano-4-chloroquinoline is heated with 19 g of thienylmethylamine at 115° C. for 4 hours. The reaction mixture is cooled to 25° C. and mixed 6 times with 50 ml of water. The crystals are filtered off, washed 2 times with 50 ml of water and dried. The resulting product is recrystallized from 60 ml of N,N-dimethylformamide, to obtain 6.8 g pale yellow title compound, m.p.: 208-209° C.

NMR, $\delta_H$ (200 MHz, DMSO-$d_6$): 5.18 ppm (d, 2H, Thienyl-CH$_2$), 6.28 ppm (s, 2H), 6.96-7.00 ppm (m, 1H), 7.07-0.19 ppm (m, 2H), 7.31-7.42 ppm (m, 2H), 7.48-7.56 ppm (m, 1H), 8.09-8.13 ppm (m, 1H), 8.30 ppm (t, 1H).

b. Ethyl 9-thienylamino-10-cyano-imidazo[1,2-a]quinoline-2-carboxylate

To the solution of 5.61 g of 2-amino-3-cyano-4-thienylaminoquinoline in 200 ml of abs. ethanol, 4.29 g of ethyl bromopyruvate is added at 70° C. under stirring. The reaction mixture is heated under reflux for 2 hours and the precipitated crystals are filtered off to obtain 2.54 g of the title compound. M.p.: 255-256° C.

NMR, $\delta_H$ (200 MHz, DMSO-$d_6$): 1.33 ppm (t, 3H, COOCH$_2$CH$_3$), 4.31 ppm (q, 2H, COOCH$_2$CH$_3$), 5.24 ppm (d, 2H, Thienyl-CH$_2$), 6.96-7.00 ppm (m, 1H), 7.14 ppm (m, 1H), 7.40-7.43 ppm (m, 1H), 7.61-7.68 ppm (m, 1H), 7.82-7.90 ppm (m, 1H), 8.42-8.46 ppm (m, 3H), 9.05 ppm (s, 1H, 3-H).

c. 9-Thienylamino-10-cyano-imidazo[1,2-a]quinoline-2-carboxylic acid

The mixture of 2.54 g of ethyl 9-thienylamino-10-cyano-imidazo[1,2-a]quinoline-2-carboxylate, 40 ml of ethanol and 33 ml of 10% sodium hydroxide is stirred at 25° C. for 6 hours. To the thick suspension 80 ml of water is added and with 96% acetic acid the mixture acidified to pH=3. The pale yellow crystals are filtered off, washed 5 times with 10 ml of water and dried. 2.18 g of the title compound is obtained, m.p.: 209-217° C. under decomposition.

NMR, $\delta_H$ (400 MHz, DMSO-$d_6$): 5.24 ppm (d, 2H, Thienyl-CH$_2$), 8.88 ppm (s, 1H, 3-H).

d. 1-(9-Thienylamino-10-cyano-imidazo[1,2-a]quinoline-2-carbonyl)morpholine

To the mixture of 1.80 g of 9-thienylamino-10-cyano-imidazo[1,2-a]quinoline-2-carboxylic acid and 1.1 ml of triethylamine in 10 ml of chloroform, the solution of 0.87 g of pyvaloyl chloride in 10 ml of chloroform is added dropwise, under stirring at 5° C., in a period of 15 minutes. The reaction mixture is stirred at 5° C. for 1 hour, then the mixture of 0.61 g of morpholine, 10 ml of chloroform and 1.1 ml of triethylamine is added to it. The mixture is stirred at 25° C. for 3 hours, diluted with 100 ml of chloroform, extracted consecutively with 50 ml of water, 50 ml of 5% sodium hydrogen carbonate solution and 50 ml of water, dried over sodium sulfate and concentrated in vacuum. The yellow crystalline material is recrystallized from 200 ml of ethanol. 0.19 g of the title compound is obtained, m.p.: 315° C.

NMR, $\delta_H$ (400 MHz, DMSO-$d_6$): 3.6 ppm (m, 6H), 4.2 ppm (m, 2H), 5.24 ppm (d, 2H, Thienyl-CH$_2$), 6.97-7.00 ppm (m, 1H), 7.14 ppm (m, 1H), 7.41 ppm (m, 1H), 7.61-7.65 ppm (m, 1H), 7.83-7.87 ppm (m, 1H), 8.37-8.45 ppm (m, 3H), 8.82 ppm (s, 1H, 3-H).

Example 7

1-(9-Thienylamino-10-cyano-imidazo[1,2-a]quinoline-2-carbonyl)piperazine

In the general formula (I) $R^1$ and $R^2$ stand for hydrogen atom, $R^3$ for 2-thienyl group, $R^4$, $R^5$, $R^6$ and $R^7$ for hydrogen atom, $R^8$ for cyano group, X means —NH— group, Z means —NH— group, the value of n is 1, the value of m and o is 2, and the value of r and p is 0.

To the mixture of 1.80 g of 9-thienylamino-10-cyano-imidazo[1,2-a]quinoline-2-carboxylic acid—obtained as described in Example 6—and 1.1 ml of triethylamine in 10 ml of chloroform, the solution of 0.87 g of pyvaloyl chloride in 10 ml of chloroform is added dropwise, under stirring at 5° C., in a period of 15 minutes. The reaction mixture is stirred at 5° C. for 1 hour, then the mixture of 0.61 g of piperazine, 10 ml of chloroform and 1.1 ml of triethylamine is added to it. The mixture is stirred at 25° C. for 3 hours, diluted with 100 ml of chloroform, extracted consecutively with 50 ml of water, 50 ml of 5% sodium hydrogen carbonate solution and 50 ml of water, dried over sodium sulfate and concentrated in vacuum. The pale yellow crystalline material is recrystallized from 50 ml of ethanol. 0.19 g of the title compound is obtained, m.p.: 269° C.

NMR, $\delta_H$ (400 MHz, DMSO-$d_6$): 2.7 ppm (m, 4H), 3.5 ppm (m, 2H), 4.05 ppm (m, 2H), 5.24 ppm (d, 2H, Thienyl-CH$_2$), 6.97-7.00 ppm (m, 1H), 7.14 ppm (m, 1H), 7.41 ppm (m, 1H), 7.61-7.65 ppm (m, 1H), 7.83-7.87 ppm (m, 1H), 8.37-8.45 ppm (m, 3H), 8.82 ppm (s, 1H, 3-H).

Structure and physical parameters of the compounds of the formula (III) prepared according to Example 1. is demonstrated in Table I.

TABLE I (III)

[Structure: quinoline fused with imidazole; R³–(CR¹R²)ₙ–X– substituent at position bearing CN; ethyl ester –C(O)OC₂H₅ on imidazole ring]

| No. | R¹ | R² | R³ | X | n | Mp [°C] |
|---|---|---|---|---|---|---|
| 8. | Me (wedge) | H | phenyl | NH | 1 | 146 |
| 9. | Me (dash) | H | phenyl | NH | 1 | 145 |
| 10. | H | H | 2,3-dimethoxyphenyl (OMe, OMe) | NH | 2 | 34 |
| 11. | H | H | phenyl | NH | 2 | 32 |
| 12. | — | — | cyclohexyl | NH | 0 | 250 |
| 13. | — | — | cyclopentyl | NH | 0 | 128 |
| 14. | H | H | 4-methoxyphenyl | NH | 1 | 45 |
| 15. | H | H | 2-methoxyphenyl | NH | 1 | 54 |
| 16. | H | H | phenyl | O | 1 | 185 |

TABLE I-continued (III)

| No. | R¹ | R² | R³ | X | n | Mp [°C] |
|---|---|---|---|---|---|---|
| 17. | H | H | phenyl | S | 1 | 190 |
| 18. | H | H | phenyl | S=O | 1 | 230 |
| 19. | H | H | phenyl | O=S=O | 1 | 255 |

Structure and physical parameters of the compounds of the formula (IV) prepared according to Example 1. is demonstrated in Table II.

TABLE II (IV)

[Structure: 2-amino-3-cyano-4-substituted quinoline with R⁵, R⁶ on benzo ring; substituent X–(CR¹R²)ₙ–R³ at position 4]

| No. | R¹ | R² | R³ | R⁵ | R⁶ | X | n | Mp [°C] |
|---|---|---|---|---|---|---|---|---|
| 20. | H | H | 2-methoxyphenyl | H | H | NH | 1 | 192 |
| 21. | H | H | 4-methoxyphenyl | H | H | NH | 1 | 202 |
| 22. | H | H | 2-thienyl | I | H | NH | 1 | 198 |

TABLE II-continued

(IV)

| No.: | R¹ | R² | R³ | R⁵ | R⁶ | X | n | Mp [° C.] |
|---|---|---|---|---|---|---|---|---|
| 23. | H | H | 4-MeO-C₆H₄ | H | H | NH | 1 | 167 |
| 24. | H | Me (wedge) | C₆H₅ | H | H | NH | 1 | 182 |
| 25. | H | Me (dash) | C₆H₅ | H | H | NH | 1 | 183 |
| 26. | H | H | C₆H₅ | H | H | NH | 2 | 172 |
| 27. | H | H | 3,4-(MeO)₂-C₆H₃ | H | H | NH | 2 | 143 |
| 28. | H | H | C₆H₅ | H | H | N-Me | 1 | 212 |
| 29. | H | H | C₆H₅ | H | H | S | 1 | 168 |
| 30. | H | H | C₆H₅ | H | H | O | 1 | 213 |
| 31. | H | H | C₆H₅ | Cl | H | NH | 1 | 234 |
| 32. | H | H | 2-furyl | Cl | H | NH | 1 | 221 |
| 33. | H | H | C₆H₅ | Me | H | NH | 1 | 198 |
| 34. | H | H | C₆H₅ | MeO | H | NH | 1 | 201 |
| 35. | H | H | C₆H₅ | H | Cl | NH | 1 | 191 |
| 36. | H | H | C₆H₅ | OH | H | NH | 1 | 246 |
| 37. | H | H | 3-I-C₆H₄ | H | H | NH | 1 | 227 |
| 38. | H | H | 2-thienyl | MeO | H | NH | 1 | 217 |
| 39. | H | H | 2-thienyl | Me | H | NH | 1 | 198 |
| 40. | H | H | 2-thienyl | Cl | H | NH | 1 | 168 |
| 41. | H | H | C₆H₅ | H | H | NH | 0 | 214 |

Structure and physical parameters of the compounds of the formula (V) prepared according to Example 1. is demonstrated in Table III.

TABLE III

| No: | R⁴ | R⁵ | R⁶ | R⁷ | Mp [° C.] |
|---|---|---|---|---|---|
| 42. | H | OH | H | H | 360 |
| 43. | H | Cl | H | H | 250 |
| 44. | H | H | Cl | H | 278 |
| 45. | H | Me | H | H | 283 |
| 46. | H | OMe | H | H | 360 |
| 47. | H | H | H | OMe | 234 |

TABLE III-continued

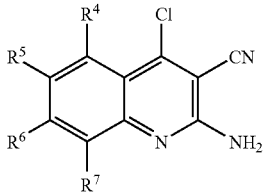

| No: | R⁴ | R⁵ | R⁶ | R⁷ | Mp [° C.] |
|---|---|---|---|---|---|
| 48. | Me | H | H | H | 246 |
| 49. | H | H | H | Me | 267 |
| 50. | H | I | H | H | 293 |

Example 51

The tablet of the following composition is prepared by known methods:

| | |
|---|---|
| Active ingredient: | 25 mg |
| Lactose | 50 mg |
| Avicel | 21 mg |
| Crospovidone | 3 mg |
| Magnesium stearate | 1 mg |

Biology
Methods
Human Adenosine $A_3$ Receptor Binding

Preparing membrane suspension: ovarium cells of cloned golden hamster expressing human $A_3$ receptor (further: CHO-$hA_3$) are appropriately cultured and propagated. Achieving confluent cell layer, the culturating liquid is removed from the cells by washing them with 37° C. PBS, then the cell are suspended in ice cold PBS, centrifuged (1000×g 10 perc) (Sigma 3K30) and homogenated using teflon homogenizer (B. Braun Potter S) at 1500/min rotation speed, for 15 sec. in the following buffer: 50 mM Tris, 10 mM $MgCl_2$, 1 mM EDTA, pH 8.0. The homogenatum is centrifuged (43.000 g, 10 min). The precipitate is suspended in the above buffer, protein concentration 0.1 mg/ml (Bradford method). Aliquots of the membrane preparatum are stored at −80° C.

Binding protocol: incubate CHO-$hA_3$ membrane preparation (2 μg protein content) in incubation buffer (50 mM Tris, 10 mM $MgCl_2$, 1 mM EDTA, 3 U/mL adenosine deaminase, pH 8.0), in the presence of 0.5 nM [$^{125}$I]AB-MECA (p-amino-3-iodo-benzyl-5'-N-methylcarboxamido-adenosine) (100.000 cpm) and 100 μM R-PIA ($N^6$-[L-2-phenyliso-propyl]adenosine) to define non-specific binding of test compound in a total volume of 50 μL for 1 hr at room temperature. Filter over Whatman GF/B glass fibre filters (presoaked in 0.5% polyethylenimine for 3 hours), wash 4× with 1 mL ice-cold 50 mM Tris, 10 mM $MgCl_2$, 1 mM EDTA (pH 8.0) on 96-well Brandel Cell Harvester. Detection of activity: in gamma-counter (1470 Wizard, Wallac). Inhibition [%]=100−((activity in the presence of test compound−non-specific activity)/(total activity−non-specific activity))*100.

Human Adenosine $A_1$ Receptor Binding

Preparing membrane suspension: ovarium cells of cloned golden hamster expressing human $A_1$ receptor (further: CHO-$hA_1$) are appropriately cultured and propagated. Achieving confluent cell layer the culturating liquid is removed from the cells by washing them with 37° C. PBS, then the cell are suspended in ice cold PBS, washed 3 times with ice cold PBS, centrifuged (1000×g 10 perc) (Sigma 3K30) and homogenated using teflon homogenizer (B. Braun Potter S) at 1500/min rotation speed, for 15 sec. in the following buffer: 50 mM Tris, 10 mM HCl, pH 7.4. The homogenatum is centrifuged (43.000 g, 10 min). The precipitate is suspended in the above buffer, protein concentration 5 mg/mL (Bradford method). Aliquots of the membrane preparatum are stored at −80° C.

Binding protocol: incubate CHO-$hA_1$ membrane preparation (50 μg protein content) in incubation buffer (50 mM Tris, 3 U/mL adenosine deaminase, pH 7.4), 10 nM [$^3$H]CCPA (2-chloro-$N^6$-cyclopenthyl-adenosine) (80.000 dpm) and 10 μM R-PIA ($N^6$-[L-2-phenylisopropyl]adenosine) to define the non-specific binding or test compound in a total volume of 100 μL for 3 hr at room temperature. Filter over Whatman GF/B glass fibre filters (presoaked in 0.5% polyethylenimine for 3 hours), wash 4× with 1 mL ice-cold 50 mM Tris (pH 7.4) on 96-well Brandel Cell Harvester. Detection of activity: in the presence of 200 μL of HiSafe-3 cocktail in beta-counter (1450 Microbeta, Wallac). Inhibition [%]=100−((activity in the presence of test compound−non-specific activity)/(total activity−non-specific activity))*100.

Human Adenosine $A_{2a}$ Receptor Binding

Binding protocol: Incubate 7 μg of membranes (human $A_{2a}$ adenosine receptors transfected into HEK-293 cells, source: Receptor Biology, Inc.), buffer (50 mM Tris-HCl, 10 mM $MgCl_2$, 1 mM EDTA, 2 U/mL adenosine deaminase, pH 7.4), 20 nM [$^3$H]CGS-21680 (2-[p-(2-carbonylethyl)phenylethy-lamino]-5'-N-ethylcarboxamido-adenosine) (200.000 dpm) and 50 μM NECA (5'-N-ethylcarboxamido-adenosine) to define the non-specific binding of test compound, in a total volume of 100 μl for 90 min at room temperature. Filter in vacuum over Whatman GF/B glass fibre filters (presoaked for 3 hours in 0.5% polyethylenimine), wash 4× with 1 mL ice-cold 50 mM Tris, 10 mM $MgCl_2$, 1 mM EDTA, 0.9% NaCl, pH 7.4) on 96-well Brandel Cell Harvester. Detection of activity: in beta-counter (1450 Microbeta, Wallac) in the presence of 200 μL of HiSafe-3 cocktail. Inhibition [%]=100−((activity in the presence of test compound−non-specific activity)/(total activity−non-specific activity))*100.

Human Adenosine $A_{2b}$ Receptor Binding

Binding protocol: incubate 20.8 μg of membranes (human $A_{2b}$ adenosine receptors transfected into HEK-293 cells, source: Receptor Biology, Inc.), buffer (50 mM Tris-HCl, 10 mM $MgCl_2$, 1 mM EDTA, 0.1 mM benzamidine, 2 U/mL adenosine deaminase, pH 6.5), 32.4 nM [$^3$H]DPCPX (8-cyclopenthyl-1,3-dipropylxanthine) (800.000 dpm) and 100 μM NECA (5'-N-ethylcarboxamido-adenosine) to define non-specific binding or test compound in a total volume of 100 μL for 30 min at room temperature. Filter under 25 Hgmm vacuum over Whatman GF/C glass fibre filters (presoaked in 0.5% polyethylenimine for 3 hours), wash 4× with 1 mL ice-cold 50 mM Tris-HCl (pH 6.5) on 96-well Brandel Cell Harvester. Detection of activity: in the presence of 200 μL of HiSafe-3 cocktail in beta-counter (1450 Microbeta, Wallac). Inhibition [%]=100−((activity in the presence of test compound−non-specific activity)/(total activity−non-specific activity))*100

Results

We consider the compounds as biologically actives ones if they inhibit the binding of the radioligand on human adenosine $A_3$ receptors with an activity above 80% at 1 μM in our experimental conditions.

The dissociation constant ($K_d$) of [$^{125}$I]AB-MECA on CHO-$hA_3$ membrane preparation is determined by isotope saturation studies with the help of Scatchard analysis (G. Scatchard, Ann. N.Y. Acad. Sci. 51:660, 1949). The $IC_{50}$ is converted to an affinity constant ($K_i$) by application of the Cheng-Prusoff equation (Y. J. Cheng and W. H. Prusoff, Biochem. Pharmacol. 22:3099, 1973).

Several compounds of the general formula (I), (II), (III), (IV) and (V) display remarkable biological effects. Most important activities are exhibited by the compounds of the general formula (I) defined in claims 1-3. Especially advantageous are the compounds given in the Examples, their $K_i$ values are in the range of 0.8 nM and 700 nM. $K_i$ values of the most advantageous compounds are 0.8 and 15 nM.

The compounds possess proper bioavailability and a selectivity of at least 3 order of magnitude, in respect of the human adenosine $A_1$, $A_{2a}$ and $A_{2b}$ receptor subtypes.

Further, the duration of their action at intravenous and oral administration is long, their $ED_{50}$ values are low, their toxicological and side-effect profiles are advantageous.

These above data favour the therapeutic application of the compounds of the general formula (I).

We claim:

1. A compound of formula (I)

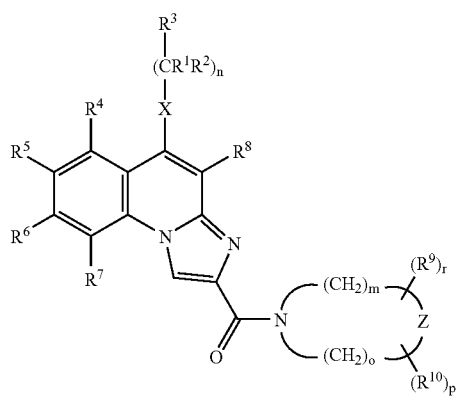

(I)

wherein:
$R^1$ is hydrogen or straight or branched $C_{1-4}$ alkyl;
$R^2$ is hydrogen or straight or branched $C_{1-4}$ alkyl;
$R^3$ is hydrogen, straight or branched $C_{1-4}$ alkyl, $C_{3-6}$ cycloalkyl,
  phenyl, thienyl, or furyl, wherein the phenyl, thienyl, or furyl is optionally substituted with one or more straight or branched $C_{1-4}$ alkyl, straight or branched $C_{1-4}$ alkoxy, or halogen,
  a six- or five-membered heteroaromatic ring containing one, two or three nitrogen, wherein the heteroaromatic ring is optionally substituted by one or more straight or branched $C_{1-4}$ alkyl, straight or branched $C_{1-4}$ alkoxy, or halogen, or
  a five-membered heteroaromatic ring containing one nitrogen atom and one oxygen atom, or one nitrogen atom and one sulphur atom, wherein the heteroaromatic ring is optionally substituted by one or more straight or branched $C_{1-4}$ alkyl, straight or branched $C_{1-4}$ alkoxy, or halogen;
$R^4$, $R^5$, $R^6$ and $R^7$ are independently hydrogen, straight or branched $C_{1-4}$ alkyl, straight or branched $C_{1-4}$ alkoxy, hydroxy or halogen, or
$R^4$ and $R^7$ are both hydrogen, and $R^5$ and $R^6$ taken together form methylenedioxy;
$R^8$ is hydrogen, cyano, aminocarbonyl, $C_{1-4}$ alkoxycarbonyl, or carboxy;

$R^9$ and $R^{10}$ are each, independently, hydrogen, straight or branched $C_{1-4}$ alkyl, or $C_{3-6}$ cycloalkyl;
X is —$CH_2$—, —NH—, —$NR^{11}$—, —S—, —O—, —S(O)— or —$S(O)_2$—;
$R^{11}$ is straight or branched $C_{1-4}$ alkyl or $C_{3-6}$ cycloalkyl;
Z is —S—, —NH— or —$NR^{12}$—;
$R^{12}$ is straight or branched $C_{1-4}$ alkyl or $C_{3-6}$ cycloalkyl;
n is zero, 1 or 2;
m is zero, 1, 2 or 3
o is zero, 1, 2 or 3, provided that at least one of m and o is different from zero;
p is zero or 1; and
r is zero or 1;
or a geometric or optically active isomer, or salt thereof, or a salt of the geometric or optically active isomer thereof.

2. The compound according to claim 1, wherein
$R^3$ is hydrogen, straight or branched $C_{1-4}$ alkyl, $C_{3-6}$ cycloalkyl, or
  phenyl, thienyl, or furyl, wherein the phenyl, thienyl, or furyl is optionally substituted with one or more straight or branched $C_{1-4}$ alkyl, straight or branched $C_{1-4}$ alkoxy, or halogen,
or a geometric or optically active isomer, or salt thereof, or a salt of the geometric or optically active isomer thereof.

3. The compound according to claim 1, wherein
$R^1$ is hydrogen or methyl;
$R^2$ is hydrogen or methyl;
$R^3$ is phenyl, thienyl or furyl;
$R^8$ is hydrogen or cyano;
$R^9$ and $R^{10}$ are independently hydrogen, methyl, ethyl or cyclopropyl;
X is —NH— or —O—;
n is 1;
m and o are 2; and
p and r are zero,
or a geometric or optically active isomer, or salt thereof, or a salt of the geometric or optically active isomer thereof.

4. The compound according to claim 1, which is
1-(9-Benzylamino-10-cyano-imidazo[1,2-a]quinoline-2-carbonyl)-4-methylpiperazine;
1-(9-Furfurylamino-10-cyano-imidazo[1,2-a]quinoline-2-carbonyl)-4-methylpiperazine;
1-(9-Furfurylamino-10-cyano-imidazo[1,2-a]quinoline-2-carbonyl)piperazine; or
1-(9-Thenylamino-10-cyano-imidazo[1,2-a]quinoline-2-carbonyl)piperazine,
or a geometric or optically active isomer, or salt thereof, or a salt of the geometric or optically active isomer thereof.

5. A process for preparing the compound according to claim 1, comprising acylating a compound of formula (VIII)

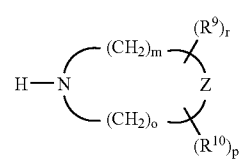

VIII wherein $R^9$, $R^{10}$, Z, m, o, p and r are as defined in claim 1, with an acid of formula (II)

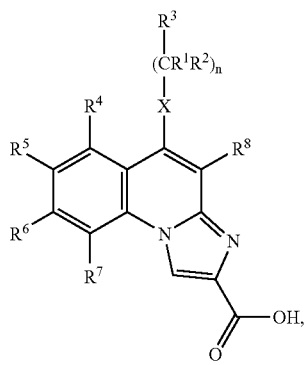

wherein $R^1$, $R^2$, $R^3$, $R^4$, $R^5$, $R^6$, $R^7$, $R^8$, X, and n are as defined in claim 1.

6. The process according to claim 5, wherein the acylating is carried out in the presence of a base, in an organic solvent.

7. The process according to claim 6, wherein the organic solvent is a halogenated Hydrocarbon.

8. The process according to claim 7, wherein the organic solvent is chloroform.

9. The process according to claim 6, wherein the base is an organic base.

10. The process according to claim 9, wherein the base is triethylamine.

11. A pharmaceutical composition comprising a pharmaceutically effective amount of the compound according to claim 1, or a geometric or optically active isomer, or salt thereof, or a salt of the geometric or optically active isomer thereof, and one or more auxiliary materials.

12. A pharmaceutical composition comprising a pharmaceutically effective amount of the compound according to claim 3, or a geometric or optically active isomer, or salt thereof, or a salt of the geometric or optically active isomer thereof, and one or more auxiliary materials.

* * * * *